United States Patent [19]

Itoh

[11] Patent Number: 4,982,553
[45] Date of Patent: Jan. 8, 1991

[54] AUTOMATIC TEST TUBE PLUG EXTRACTION APPARATUS

[76] Inventor: Teruaki Itoh, 5-25, Kokaihonmachi, Kumamoto-shi, Kumamoto-Ken 860, Japan

[21] Appl. No.: 137,855
[22] PCT Filed: Mar. 31, 1987
[86] PCT No.: PCT/JP87/00199
 § 371 Date: Nov. 30, 1987
 § 102(e) Date: Nov. 30, 1987
[87] PCT Pub. No.: WO87/06709
 PCT Pub. Date: Nov. 5, 1987

[30] Foreign Application Priority Data

Apr. 30, 1986 [JP] Japan .................................. 61-66703
Apr. 30, 1986 [JP] Japan .................................. 61-66705
Aug. 27, 1986 [JP] Japan .................................. 61-131705

[51] Int. Cl.⁵ ........................ B65B 35/36; B65B 43/40
[52] U.S. Cl. ........................................ 53/246; 53/251;
 53/381 A; 53/534; 29/235; 29/252; 198/346.2;
 198/433; 198/465.1; 414/222; 414/411;
 414/416
[58] Field of Search .................... 29/426.3, 426.5, 823,
 29/235, 252; 53/50, 158, 246, 247, 249, 381 A,
 468, 475, 492, 539, 534, 251; 198/346.2, 433,
 465.1, 465.2, 465.3; 269/54.2, 54.3; 414/222,
 225, 441, 416

[56] References Cited

U.S. PATENT DOCUMENTS

| | | | |
|---|---|---|---|
| 2,967,633 | 1/1961 | Stegemann et al. | 414/416 |
| 3,115,966 | 12/1963 | Leiter | 198/346.2 |
| 3,520,102 | 7/1970 | Hinrion | 53/381 A X |
| 3,796,544 | 3/1974 | Zauft et al. | 422/66 |
| 3,844,428 | 10/1974 | Olsen | 198/346.2 X |
| 4,217,798 | 8/1980 | McCarthy et al. | 53/381 A X |
| 4,244,458 | 1/1981 | Kampf | 198/346.2 |
| 4,522,089 | 6/1985 | Alvi | 53/381 A X |
| 4,687,093 | 8/1987 | Marshall et al. | 198/465.2 |
| 4,850,470 | 7/1989 | Ferkany | 198/465.2 X |

FOREIGN PATENT DOCUMENTS

| | | |
|---|---|---|
| 3430170 | 2/1986 | Fed. Rep. of Germany . |
| 2303738 | 3/1975 | France . |
| 53-49479 | 4/1978 | Japan . |
| 2058028 | 4/1981 | United Kingdom . |

Primary Examiner—Robert L. Spruill
Assistant Examiner—Linda B. Johnson
Attorney, Agent, or Firm—Nixon & Vanderhye

[57] ABSTRACT

A rack, with a plurality of test tubes arranged on it, in m columns and n rows, is transported into a main housing by a rack-inlet mechanism. In the main housing, tube-extracting mechanism extracts the tubes from rack, row by row, while the rack is being transported by a rack-transporting mechanism. The tubes are then conveyed, one by one, by a tube-conveying mechanism. A plug-extracting mechanism pulls each test tube conveyed by the mechanism and the plug closing this tube, away from each other, while holding the tube and the plug, thereby extracting the plug from the test tube. The test tubes are further conveyed by the tube-conveying mechanism after the plugs have been extracted from them. The tubes are then inserted by a tube-inserting mechanism row by row, into a vacant rack transported by the rack-transporting mechanism. After a predetermined number of rows of test tubes have been inserted into this rack, a rack-outlet mechanism transports the rack from said main housing.

4 Claims, 6 Drawing Sheets

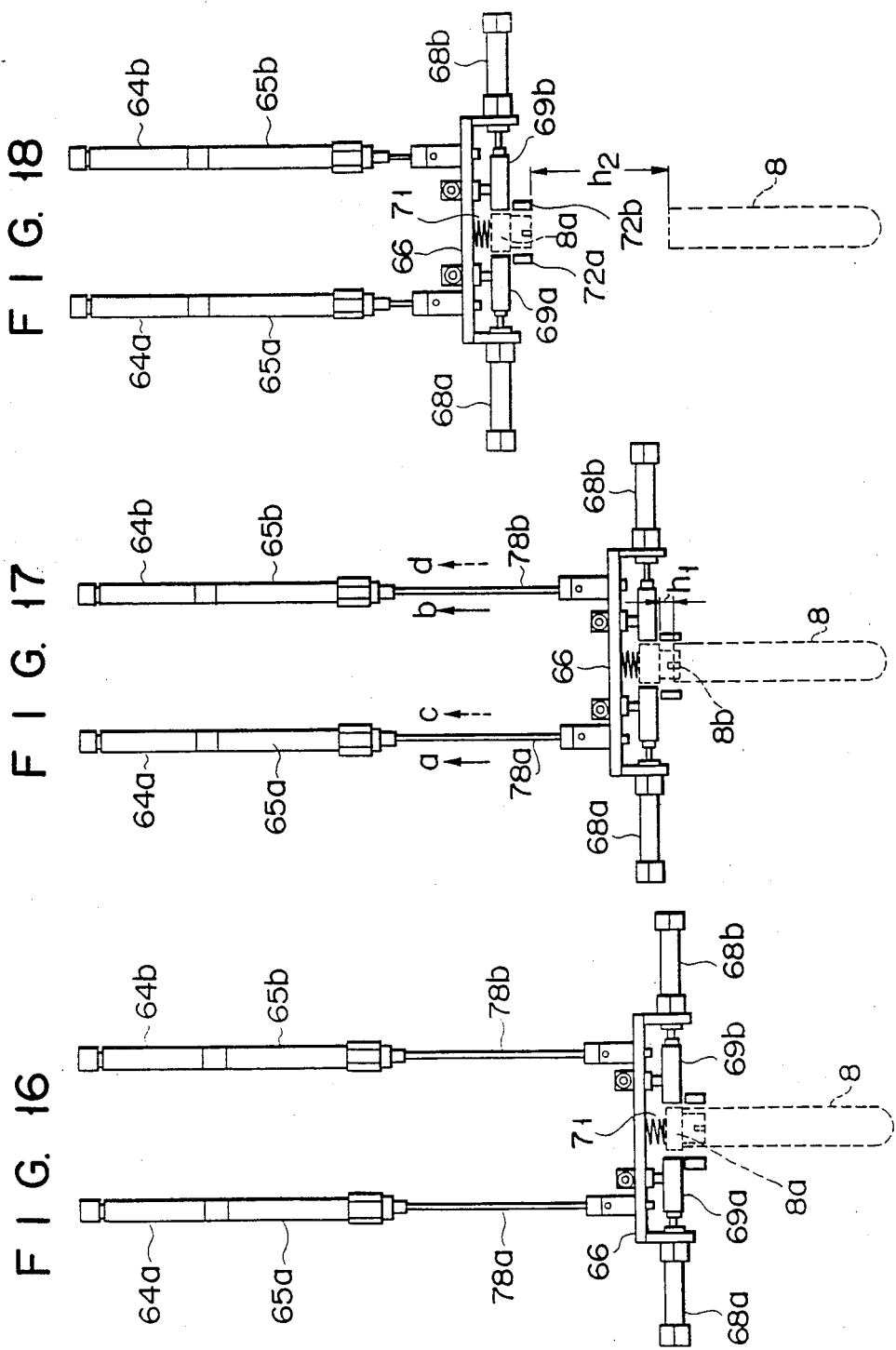

AUTOMATIC TEST TUBE PLUG EXTRACTION APPARATUS

TECHNICAL FIELD

The present invention relates to an apparatus for automatically extracting plugs from test tubes containing test fluid such as sampled blood

BACKGROUND ART

In order to analyze a fluid, such as blood, filled in a plugged test tube, thereby to determine the presence or absence of bacilli in the fluid, or to identify the bacilli, if any in the fluid, it is necessary to extract the plug, such as a rubber plug, from test tube, and then to divide the fluid into several portions, and finally to supply these portions to various devices for analyzing different test items. As for such analysis devices, research has been made. Analysis devices using high technology have been developed and put to a practical use. However, so-called "pre-processes," such as extraction of plugs, depend exclusively on handwork as is seen in big hospitals. A person takes plugged test tubes containing samples of blood, one by one, and then pulls the plugs therefrom. No apparatuses which can automatically extract plugs from test tubes have been provided.

The plug-extracting process, performed by handwork, is accompanied by the possibility that the fluid is split from the tube by mistake when the plug is pulled from the tube, thus wetting the person's hands, dripping onto the floor. The process is also accompanied by the possibility that the test tube is dropped onto the floor and is broken. If these undesirable events happen, the sanitary condition of the room, where this process is carried out, will be impaired. Further, the plug extraction by hand is not efficient. When a great number of test tubes must be opened within a limited time, many persons must work on this process. If sufficient labor force is not acquired, much time is required to complete the plug-extracting process.

It is accordingly the object of the present invention to provide an automatic test tube plug extraction apparatus which can readily extract plugs from test tubes without spilling the fluid from the tubes, wetting a person's hands with the fluid, dripping the fluid onto the floor, or dropping the test tubes onto the floor, thereby preserving the sanitary condition of the room where the plug-extracting process is performed, and which can extract plugs from a great number of test tubes within a short time.

DISCLOSURE OF THE INVENTION

In order to achieve the object described above, the following measures are taken in the present invention. A rack having holes, with plugged test tubes inserted in the holes and arranged in m columns and n rows, is moved by a rack-transporting mechanism toward a main housing. While the rack is being moved toward the main housing, a tube-extracting mechanism extracts the plugged tubes, row by row, from the rack. The test tubes, thus removed from the rack, are transported one after another in a prescribed order by a tube-conveying mechanism provided in the main housing. A plug-extracting mechanism, which is also provided in the housing, pulls each tube and the plug away from each other, thereby extracting the plug from the tube. The open tubes are further transported by the tube-conveying mechanism. A desired number of columns of open tubes are transferred to a vacant rack moved by the rack-transporting mechanism to the tube-conveying mechanism. After all these open tubes have been inserted in the holes of the rack, this rack is moved away from the main housing by the rack-transporting mechanism.

The automatic plug extraction apparatus described above can automatically reliably extract plugs from test tubes, without spilling the fluid from the tubes, wetting a person's hands with the fluid, dripping the fluid onto the floor, or dropping the test tubes onto the floor, thereby preserving the sanitary condition of the room where the plug-extracting process is performed. In addition, the apparatus can extract plugs from a great number of test tubes within a short time. In other words, the present invention can provide an automatic test tube plug extraction apparatus which has advantages and which has not been known hitherto.

BRIEF DESCRIPTION OF THE DRAWINGS

FIGS. 1 to 18 show an apparatus which is one embodiment of the present invention, wherein:

FIG. 1 is a perspective view of the apparatus;

FIG. 2 is a schematic, perspective view of the conveyor-type transport path of a tube-conveying mechanism;

FIG. 3 is a side view of the conveyor-type transport path of the tube-coveying mechanism shown in FIG. 2, as seen from the left;

FIG. 4 is a perspective view of one of the tube-transporting member in the form of a hollow cylinder, which is used in the tube-conveying mechanism;

FIG. 5 is a side view of the tube-transporting member;

FIG. 6 is a front view of the tube-transporting member;

FIG. 7 is a perspective view of the tube-transporting member, with a test tube inserted in it;

FIG. 8 is a side view of the tube-transporting member mounted on the tube-conveying mechanism and holding a test tube;

FIGS. 9 and 10 are perspective and top views of a mechanism for stopping the tube-transporting members in the the tube-conveying mechanism;

FIG. 11 is a front view of the plug-extracting mechanism used in the apparatus;

FIGS. 12 to 14 are top, bottom and side views of of the tube-extracting arm of the plug-extracting mechanism;

FIG. 15 is a top view of the jig provided in the plug-extracting mechanism and used to clamp a plug; and FIGS. 16 to 18 are side views of the plug-extracting mechanism, explaining how this mechanism extracts plugs from test tubes.

BEST MODE OF CARRYING OUT THE INVENTION

Figure 1:
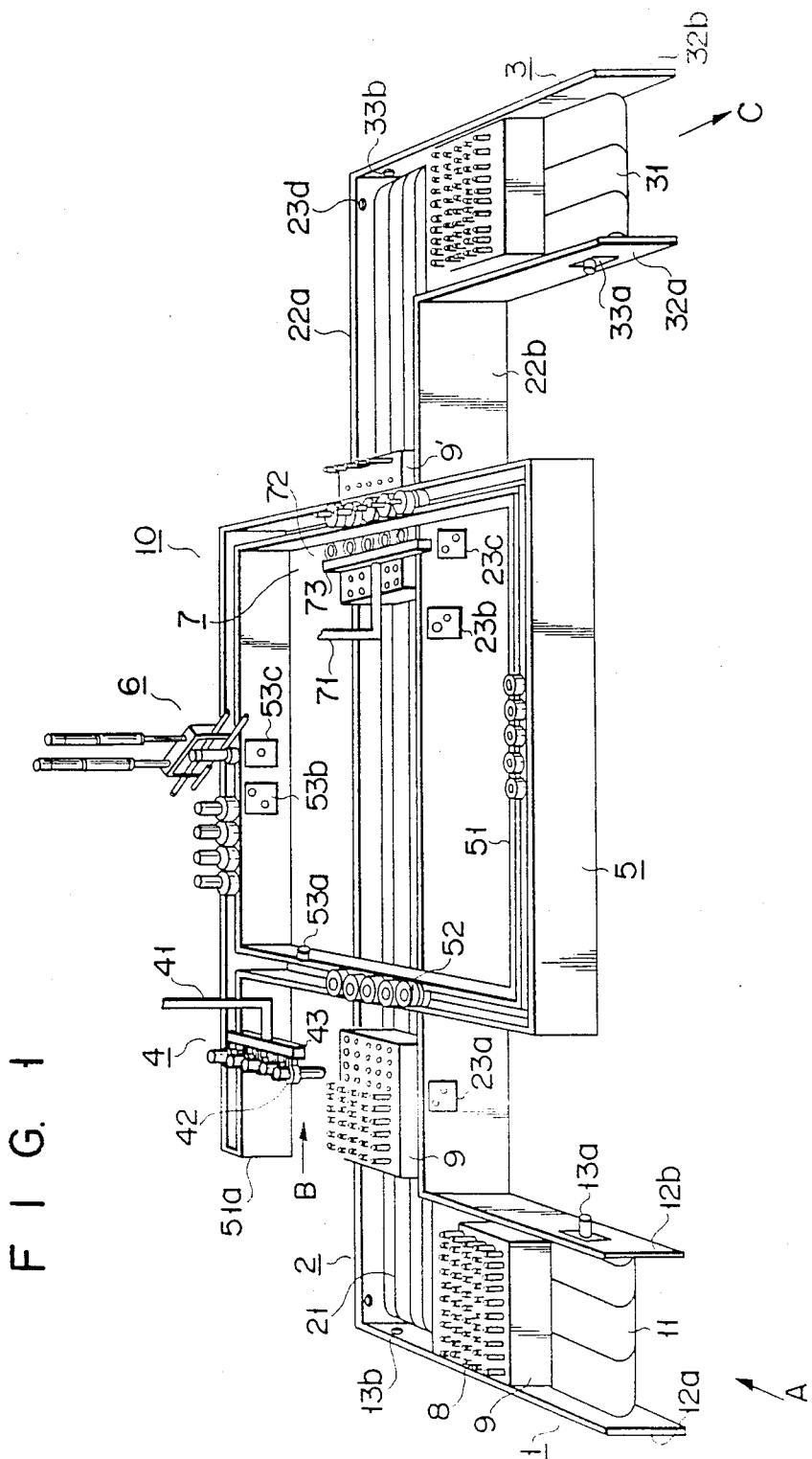

Referring to FIG. 1, numeral 1 designates a rack-inlet mechanism, numeral 2 denotes a rack-transporting mechanism, numeral 3 represents a third rack-outlet mechanism. Also in FIG. 1, numeral 4 denotes a tube-extracting mechanism, numeral 5 represents a tube-conveying mechanism for conveying tubes, numeral 6 denotes a plug-extracting mechanism, numeral 7 denotes tube-inserting mechanism. Numeral 8 denote test tubes, and numeral 9 designates racks. Numeral 10 denotes a main housing. Although not shown in FIG. 1, in main housing 10 is contained a programmable controller "FA-1J" manufactured by Izumi Denki Co., Ltd., Japan (hereinafter called "controller") for performing a sequence control of components 1 to 9.

Rack-inlet mechanism 1 is provided to transport rack 9, with test tubes 8 mounted on it and arranged in m columns and n rows, into main housing 10. (In this embodiment, tubes 8 are arranged in five columns and ten rows.) Mechanism 1 comprises belt conveyor 11 driven in the direction of arrow A, and two guide plates 12a and 12b arranged parallel to each other at both sides of belt conveyor 11. Position detectors 13a, 13b ..., such as photosensors, are provided on guide plates 12a and 12b, respectively, to detect whether or not rack 9 has been transported into main housing 10.

Rack-transporting mechanism 2 comprises belt conveyor 21 for moving rack 9 transported into main housing 10 in the direction of arrow B extending at right angles to arrow A, and guide plates 22a and 22b arranged parallel to each other at both sides of belt conveyor 21. Position detectors 23a, 23b, ..., such as photosensors, are provided on guide plates 22a and 22b to detect where rack 9 is located while it is being transported by mechanism 2. These detectors output signals when rack 9 reaches them, and these signals are used to stop and drive belt conveyor 21. Belt conveyor 21 can be replaced by a plurality of conveyors arranged one after another. In this case, it is desirable that the conveyor be located close to tube-inserting mechanism 7 and be driven in a reverse direction, whenever necessary.

Rack-outlet mechanism 3 is provided to transport rack 9 out of main housing 10. It comprises belt conveyor 31 driven in the direction of arrow C extending at right angles to arrow B and parallel to arrow A, and guide plates 32a and 32b arranged parallel to each other at both sides of belt conveyor 31. Position detectors 33a, 33b ..., such as photosensors, are provided on guide plates 32a and 32b, respectively, to detect whether or not rack 9 has been transported from the apparatus.

Tube-extracting mechanism 4 is designed to extract test tubes 8 from rack 9 moved to a specified position by rack-transporting mechanism 2 and staying in this position, row by row (that is, five tubes 8 at a time). Tube-extracting mechanism 4 comprises a drive mechanism (not shown), arm 41 which can move up and down and also in a horizontal direction when driven by the drive mechanism, and pneumatic chuck 43 coupled to the lower end of arm 41. Chuck 43 has five C-shaped hands 42 which can open and close when actuated by compressed air.

Tube-conveying mechanism 5 comprises tube-conveying path 51 shaped like a substantially square frame and having a section 51a for reversing the tube-transporting order. Tube-conveying path 51 is provided above the middle portion of rack-transporting mechanism 2 in such a position as not to prevent the passage of racks 9. Path 51 is so designed that tube-transporting members 52 can independently move in path 51. As will be described later, each of members 52 is designed to hold and stably move test tube 8 in tube-conveying path 51. Devices 53a, 53b, ... such as position detectors (e.g., photosensors) and cylinders for controlling members 52, are provided on walls constituting tube-conveying path 51. The position detectors detect the positions of tube-transporting members 52. The cylinders cooperate with the controller (not shown) to stop and move members 52 when test tubes 8 come to specified positions.

Thus, tube-conveying mechanism 5 conveys groups of tubes independently, each group consisting of five tubes 8 extracted from rack 9 by tube-extracting mechanism 4.

Plug-extracting mechanism 6 is designed to independently each test tube 8 and plug 8a closing tube 8 and extracting plug 8a from tube 8, as will later be explained in detail.

Tube-inserting mechanism 7 is adapted to insert test tubes 8, from which plugs 8a have been extracted an which have been further transported by mechanism 5, into holes cut in rack 9', row by row. Mechanism 7 comprises a drive mechanism (not shown), arm 71 which can move up and down and also in a horizontal direction when driven by the drive mechanism, and pneumatic chuck 73 coupled to the lower end of arm 71. Chuck 73 has five C-shaped hands 72 which can open and close when actuated by compressed air.

Figure 2:
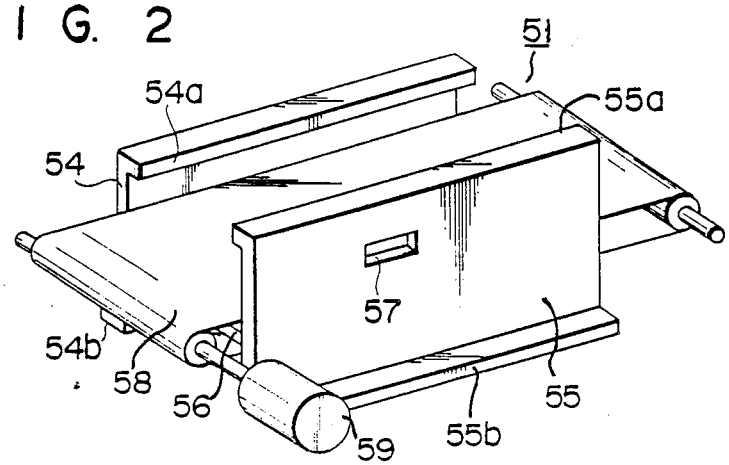
Figure 3:
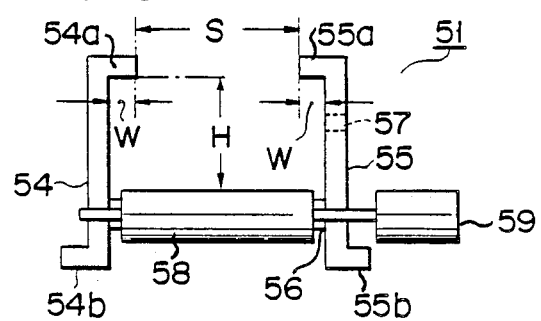

Tube-conveying path 51 of tube-conveying mechanism 5 will now be described in detail with reference to FIGS. 2 and 3. As is shown in these figures, path 51 comprises two parallel, opposing side walls 54 and 55 made of metal plates and spaced apart for a predetermined distance, and one plate 56 connecting the lower ends of side walls 54 and 55. Guide edges 54a and 55a extend from the upper ends of side walls 54 and 55, respectively, in a horizontal direction toward each other. Support legs 54b and 55b extend from the lower ends of side walls 54 and 55, respectively, in the horizontal away from each other. Slits 57 (only one shown in FIGS. 2 and 3) are cut in side walls 54 and 55. In these slits, devices 53a, 53b, ..., i.e., position detectors (e.g., photosensors) for detecting tube-transporting members 52 and cylinders for stopping members 52. Path 51 further comprises belt conveyor 58 wrapped around plate 56, which connects side walls 54 and 55. Belt conveyor 58 is driven by drive source 59 such as electric motor.

Width W of guide edges 54a and 55a, and distance S between edges 54a and 55a, and distance H between the edges 54a and 55a and upper surface of belt conveyor 58 are determined in accordance with the size and shape of tube-transporting members 52.

Figure 4:
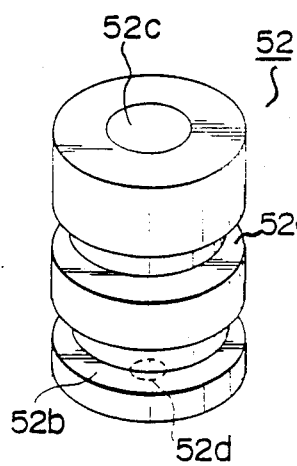
Figure 5:
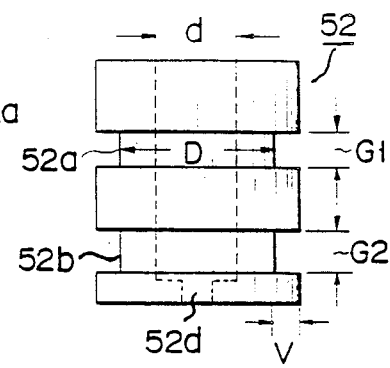
Figure 6:
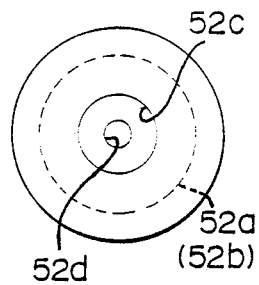

Tube-transporting members 52 will now be described with reference to FIGS. 4 to 6. As is shown in these figures, each member 52 has two annular grooves 52a and 52b cut in the circumference, and a hole 52c extending in its axial direction. Hole 52c is provided to accommodate test tube 8. The bottom of hole 52c has a small hole 52d. Width G1 of annular groove 52a is slightly greater than the thickness of guide edges 54a and 55a. Diameter D of grooved portions of member 52 is a little smaller than the distance S between guide edges 54a and 55b. Width G2 of annular groove 52b is slightly greater than the diameter of stopper pin 50a, which will later be descried in detail. Diameter d of hole 52c for accommodating test tube 8 is slightly smaller than the that of test tube 8. The diameter of hole 52d is far smaller than that of test tube 8. Depth V of annular grooves 52a and 52b is determined by the retreated position of stopper pin 50a. Annular groove 52b can be a little deeper than annular groove 52a.

Figure 7:
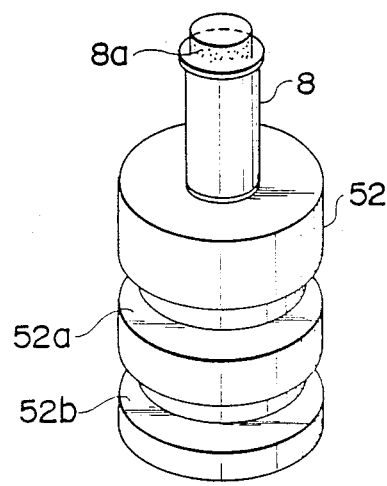
Figure 8:
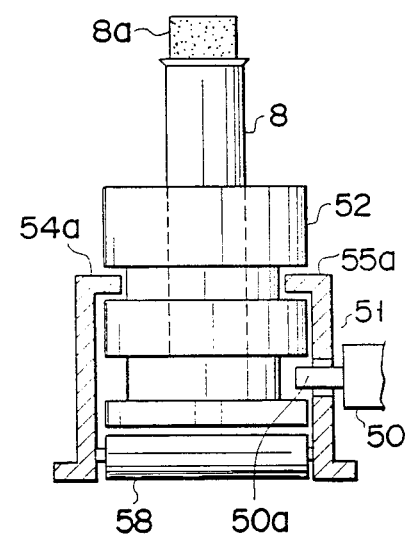
Figure 9:
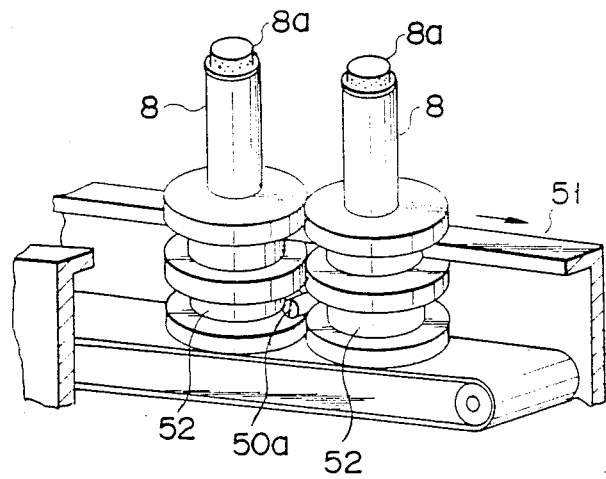
Figure 10:
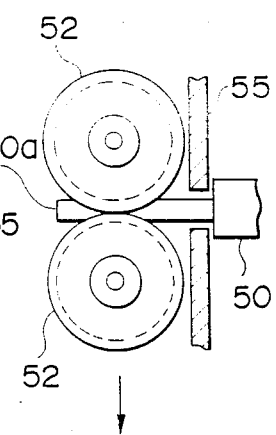

Referring to FIGS. 7 to 10, it will be explained how test tube 8 inserted in hole 52c of each tube-transporting member 52 is transported by tube-conveying mechanism 5. Member 52 holding test tube 8, as is shown in FIG. 7, is set into tube-conveying path 51 of tube-conveying mechanism 5 as is illustrated in FIG. 8. At this time, cylinder 50 provided for controlling the movement of member 52 is in its retreated position, and stopper pin 50a is therefore completely retreated. As belt conveyor 58 is driven, tube-transporting member 52 therefore is moved forward while being guided by guide edges 54a and 55a of path 51. Since guide edges 54a and 55a are inserted in annular groove 52a of member 52, member 52 is stably transported, without the possibility that it is tipped over. When cylinder 50 is actuated by the controller while members 52 are sequentially transported in path 51, stopper pin 50a thrusts into the gap between two adjacent members 52, more precisely the gap between annular grooves 52a of these members 52, as is shown in FIG. 10, thereby stopping all members 52, that are located upstream of stopper pin 50a. Even if two adjacent members 50a contact each other, stopper pin 50a can thrust into the gap between annular grooves 52a of these members 52 without separating two adjacent members 51 from each other.

Figure 11:
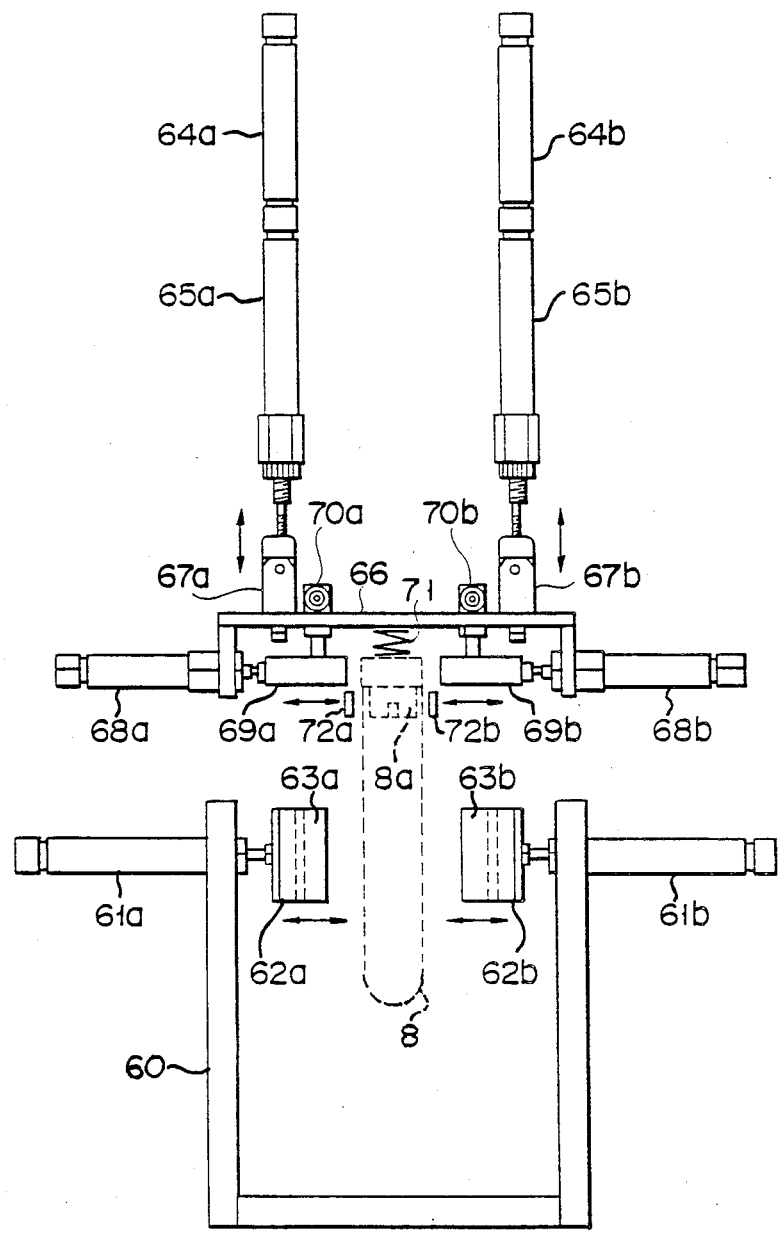
Figure 12:
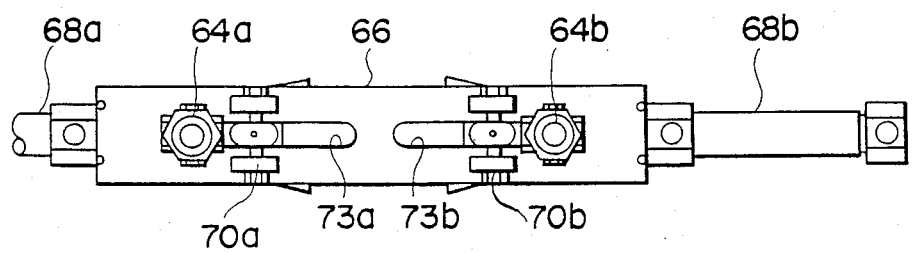

Plug-extracting mechanism 6 will now be described in detail with reference to FIGS. 11 to 15. In FIG. 11, numeral 60 designates a U-shaped, stationary frame. Two cylinders 61a and 61b for clamping test tube 8 are secured to frame 60 and axially aligned with each other. Cylinders 61a and 61b have a driven rod each. Tube-clamping members 62a and 62b are fixed to the tips of the driven rods of cylinders 61a and 61b, respectively. Elastic pads 63a and 63b are bonded to tube-clamping members 62a and 62b, respectively.

Referring to FIG. 11, numerals 64a and 64b denote a pair of plug-extracting cylinders forming a two-stroke cylinder, and numerals 64a and 65b designate a pair of plug-extracting cylinders forming another two-stroke cylinder. The upper ends of the two-stroke cylinders are supported by a support mechanism (not shown) which can be moved by the controller, when necessary. Upper cylinders 64a and 64b are simultaneously driven to pull up frame 60. Lower cylinders 65a and 65b are alternatively driven to pull up frame 60. The two-stroke cylinders have a driven rod each. The lower ends of driven rods are coupled to movable frame 66 by couplings 67a and 67b. Two cylinders 68a and 68b for clamping a plug are secured to the side walls of movable frame 66 and axially aligned with each other. Cylinders 68a and 68b have a driven rod each. Plug-clamping members 69a and 69b are fixed to the tips of the driven rods of cylinders 68a and 68b, respectively. Plug-clamping members 69a and 69b can smoothly move back and forth, guided by guide rollers 70a and 70b and also by guide grooves 73a and 73b shown in FIGS. 12 and 13. Numeral 71 denotes a coil spring provided on the lower surface of movable frame 66 and positioned at the central part thereof. This spring pushes down rubber plug 8a closing test tube 8, thereby to help styluses, which will later be described, to readily pierce plug 8a. Numerals 72a and 72b designate stopper members provided in the vicinity of plug-clamping members 69a and 69b. They are used to remove rubber plug 8a extracted from tube 8, when members 69a and 69b move backward, thus releasing plug 8a.

Figure 13:
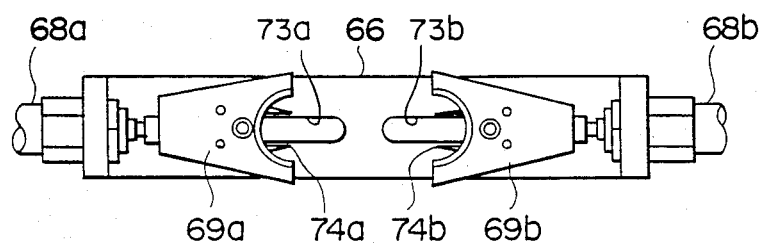
Figure 14:
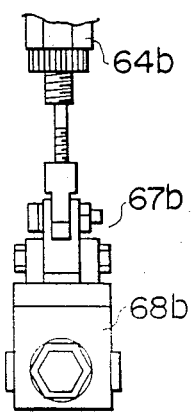
Figure 15:
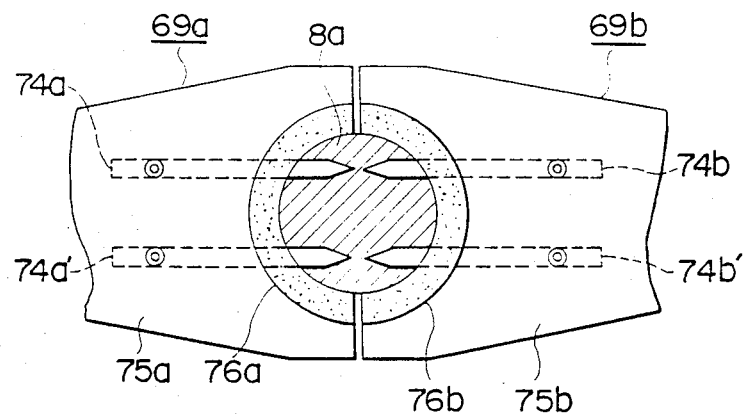

Plug-clamping members 69a and 69b have a semicircular concave each, as is shown in FIGS. 13 and 15. The semi-circular concaves are cut in the opposing sides of support plates 75a and 75b. Two styluses 74a and 74a' are secured to member 69a such that they protrude from the concave of member 69a, and two styluses 74b and 74b' and are secured to member 69b such that they protrude from the concave of member 69b. Hence, four styluses are provided in all. Elastic pads 76a and 76b are bonded to these semi-circular concaves, respectively.

When plug-clamping members 69a and 69b approach each other and touch each other, as illustrated in FIG. 15, styluses 74a and 74a' and styluses 74b and 74b' piece plug 8a, and elastic pads 76a and 76b touch the periphery of plug 8a and tightly hold plug 8a.

The operation of plug-extracting mechanism 6 will now be explained with reference to FIGS. 11 to 15 and also to FIGS. 16 to 18. When cylinders 61a and 61b, which are provided to clamp test tube 8, are operated tube 8 is clamped by tube-clamping members 62a and 62b. At this time, the periphery of tube 8 is held between elastic pads 63a and 63b. Hence, no impact is applied to tube 8, and there is no risk that tube 8 is broken.

Then, plug-extracting cylinders 64a and 65a and plug-extracting cylinders 64b and 65b are lowered, whereby driven rods 78a and 78b thrust downward. As a result, the arm as a whole moves downwardly. When the arm reaches a prescribed position, coil spring 77 abuts on the top of plug 8a as is shown in FIG. 16. Then, members 69a and 69b clamp plug 8a. As a result, styluses 74a and 74a' and styluses 74b and 74b' pierce plug 8a.

Thereafter, lower plug-extracting cylinders 65a and 65b are driven, whereby driven rods 78a and 78b alternately move up and down in the directions of arrows a, b, c and d as are illustrated in FIG. 17, thereby rocking the plug-extracting arm. Hence, plug 8a is easily extracted. Cylinders 65a and 65b complete the plug-extracting process when plug 8a is pulled up for distance h1, and groove 8b, which is cut in plug 8a for allowing air to flow into tube 8, reaches a position slightly above the open end of tube 8. At this time, air starts flowing into tube 8 through groove 8b, whereby the pressure within tube 8 becomes equal to atmospheric pressure. Then, upper plug-extracting cylinders 64a and 64b are simultaneously moved upward, thereby extracting plug 8a from from tube 8. Since the pressures inside and outside tube 8 have been balanced, and the torque applied on plug 8a has been reduced very much, there is no risk that the liquid contained in tube 8 should spill.

The operation of the plug extraction apparatus, which has the structure described above, will now be explained.

First, the controller is operated after rack 9 with test tubes 8 mounted on it has been set in rack-inlet mechanism 1, mechanism 1 transports rack 9 into main housing 10. In main housing 10, rack 9 is transported to tube-extracting mechanism 4 by belt conveyor 21 of rack-transporting mechanism 2. Then, the controller changes the operating mode of belt conveyor 21, and conveyor 21 starts moving rack 9 intermittently each time by a pitch of two adjacent rows of tubes. At the same time, tube-extracting mechanism 4 starts operating, thereby simultaneously extracting five tubes 8 of each row from rack 9 and then inserting these tubes into tube-transporting members 52. Members 52, now holding tubes 8, are moved forward by tube-conveying mechanism 5. Members 52 are arranged in reverse order as they first move into section 51a from a first section of path 51 and then move from section 51a into a second section of path 51, which extends at right angles to the direction of tube conveying of first section. Hence, tubes 8 are set In the reverse order. Members 52 are moved to plug-extracting mechanism 6, one by one. Mechanism 6 extracts plugs 8a from tubes 8. Plugs 8a are collected at one place, and will be further processed. Open tubes 8, still inserted in tube-transporting members 52, are transported to tube-inserting mechanism 7. Mechanism 7 stays until the five tubes of the column reach it. When the five tubes reach it, mechanism 7 starts operating, thereby transferring five tubes 8 to vacant rack 9' which has been placed in rack-transporting mechanism 2.

Vacant rack 9' is transported from rack-outlet mechanism 3 to a prescribed position by reversely driving the belt conveyors in the beginning of the operation. If rack 9, from which tubes 8 have been extracted by mechanism 4, is transported from mechanism 4 to said prescribed position while these tubes 8 are being transported in path 51, rack 9 can be used in place of rack 9'.

Since vacant rack 9' is also intermittently moved, each time for the distance between two adjacent columns of tubes, it is moved in synchronism with tube-inserting mechanism 7. Therefore, test tubes 8 are transferred to rack 9', row by row. Since tubes 8 have been arranged in the reverse order because of section 51, they are arranged on rack 9' in the same order as they have been arranged before.

After all test tubes 8 have been transferred to rack 9', his rack is transported to rack-outlet mechanism 3 by rack-transporting mechanism 2, and is then transported out of main body 10. Tube-transporting members 52, from which tubes 8 have been extracted, are returned to tube-extracting mechanism 4 by tube-conveying mechanism 5.

Plug 8a is automatically extracted from each of test tubes 8 inserted in the holes of rack 9 by the aforementioned sequence of operations. It is therefore sufficient to take test tubes 8 transported by rack-outlet mechanism 3.

Industrial Applicability

The automatic test tube plug extraction apparatus according to the present invention can automatically extract plugs from test tubes containing test fluid such as sampled blood. It can, therefore, be used to completely automate the handwork of opening pluged test tubes, which has been necessary even in big hospitals. If the apparatus of the invention is put on market, it can be bought and used to free people from the cumbersome handwork. Further, the apparatus is very desirable for sanitary reasons. Therefore, the apparatus can be said to be used widely.

What is claimed is:

1. An automatic test tube plug extraction apparatus comprising: a rack-inlet mechanism for transporting a rack into a main housing, said rack having a plurality of test tubes arranged in m columns and n rows; a rack-transporting mechanism for transporting the rack along a path provided in said main housing; a tube-extracting mechanism for extracting the test tubes from said rack, row by row, while said rack is being transported by said rack-transporting mechanism; a tube-conveying mechanism for conveying the test tubes, one by one, in a predetermined order after the test tubes have been extracted, row by row, by said tube-extracting mechanism, said tube-conveying mechanism comprising a tube-conveying path having guide edges and is designed to convey cylindrical tube holders each having an annular groove in which said guide edges are inserted; a plug-extracting mechanism for pulling each test tube conveyed by said tube-conveying mechanism and the plug closing this test tube, away from each other, while holding the test tube and the plug, thereby to extract the plug from the test tube; a tube-inserting mechanism for inserting the tubes, row by row, into a vacant rack transported by said rack-transporting mechanism, said test tubes having been further conveyed by said tube-conveying mechanism after the plugs have been extracted from them; and a rack-outlet mechanism for transporting said rack from said main housing after a predetermined number of rows of test tubes have been inserted into this rack.

2. An automatic test tube plug extraction apparatus according to claim 1, wherein said rack-transporting mechanism intermittently transports said rack, each time for a predetermined distance, when said rack is located in said tube-extracting mechanism or in said tube-inserting mechanism.

3. An automatic test tube plug extraction apparatus comprising: a rack-inlet mechanism for transporting a rack into a main housing, said rack having a plurality of test tubes arranged in m columns and n rows; a rack-transporting mechanism for transporting the rack along a path provided in said main housing; a tube-extracting mechanism for extracting the test tubes from said rack, row by row, while said rack is being transported by said rack-transporting mechanism; a tube-conveying mechanism for conveying the test tubes, one by one, in a predetermined order after the test tubes have been extracted, row by row, by said tube-extracting mechanism; a plug-extracting mechanism for pulling each test tube conveyed by said tube-conveying mechanism and the plug closing this test tube, away from each other, while holding the test tube and the plug, thereby to extract the plug from the test tube, said plug-extracting mechanism having cylinders for alternately pulling up both ends of a plug-extracting arm having a pair of plug-clamping members; a tube-inserting mechanism for inserting the tubes, row by row, into a vacant rack transported by said rack-transporting mechanism, said test tubes having been further conveyed by said tube-conveying mechanism after the plugs have been extracted from them; and a rack-outlet mechanism for transporting said rack from said main housing after a predetermined number of rows of test tubes have been inserted into this rack.

4. An automatic test tube plug extraction apparatus according to claim 3, wherein each of said plug-clamping members is a semi-circular member opposing each other, each having two styluses for piercing the plug.

* * * * *

UNITED STATES PATENT AND TRADEMARK OFFICE
CERTIFICATE OF CORRECTION

PATENT NO. : 4,982,553
DATED : January 8, 1991
INVENTOR(S) : Teruali ITOH It is certified that error appears in the above-identified patent and that said Letters Patent is hereby corrected as shown below:

ON THE TITLE PAGE

At section [30] relating to Foreign Application Priority Data, please revise so that the Japanese-originating Utility Model applications are identified with the letter "U" after the designated number as follows:

```
--      JAPAN ................61-66703(U)
        JAPAN ................61-66705(U)
        JAPAN ................61-131705(U)    ---.
```

Signed and Sealed this

Tenth Day of November, 1992

Attest:

DOUGLAS B. COMER

*Attesting Officer*      Acting Commissioner of Patents and Trademarks